(12) United States Patent
Cozzi

(10) Patent No.: US 6,896,515 B2
(45) Date of Patent: May 24, 2005

(54) METHOD FOR THE MANUFACTURE OF AN IMPRESSION-MAKING DEVICE FOR DENTAL USE AND IMPRESSION-MAKING DEVICE THUS OBTAINED

(76) Inventor: Gualtiero Cozzi, Via Francesco Nullo 13, 50137 Firenze (IT)

( * ) Notice: Subject to any disclaimer, the term of this patent is extended or adjusted under 35 U.S.C. 154(b) by 218 days.

(21) Appl. No.: 10/266,124

(22) Filed: Oct. 7, 2002

(65) Prior Publication Data

US 2003/0054316 A1 Mar. 20, 2003

Related U.S. Application Data

(63) Continuation-in-part of application No. PCT/IT01/00171, filed on Apr. 3, 2001.

(30) Foreign Application Priority Data

Apr. 7, 2000 (IT) ........................................ FI2000A0088
May 17, 2002 (IT) ........................................ FI20020053 U

(51) Int. Cl.[7] ................................................ A61C 9/00
(52) U.S. Cl. ........................................................ 433/37
(58) Field of Search ................................ D24/181, 152; 433/37, 34, 38, 41, 43, 45, 6, 214; 249/54, 164, 172; 128/861, 862

(56) References Cited

U.S. PATENT DOCUMENTS

| | | | | |
|---|---|---|---|---|
| 95,126 A | * | 9/1869 | McDonald | 433/45 |
| 1,367,627 A | * | 2/1921 | Roach | 433/37 |
| 1,369,768 A | | 3/1921 | Anderson | |
| 1,406,492 A | * | 2/1922 | Munger | 433/45 |
| 2,564,167 A | | 8/1951 | McLaughlin | |
| 2,685,736 A | * | 8/1954 | Schwartz | 433/41 |
| 3,626,594 A | * | 12/1971 | Zinner et al. | 433/45 |
| 4,413,979 A | | 11/1983 | Ginsburg et al. | |
| 5,769,633 A | * | 6/1998 | Jacobs et al. | 433/37 |

FOREIGN PATENT DOCUMENTS

| | | |
|---|---|---|
| EP | 0 950 382 | 10/1999 |
| FR | 2 374 889 | 7/1978 |
| GB | 513759 | 10/1939 |
| WO | WO 95/19741 | 7/1995 |

* cited by examiner

Primary Examiner—Todd E. Manahan
(74) Attorney, Agent, or Firm—McGlew and Tuttle, P.C.

(57) ABSTRACT

The method for the manufacture of an impression-making spoon for dental use, of the type comprising a tray for the impression-forming material and a handle for manipulation of the spoon, envisages forming the tray and the handle by means of folding of a single sheet of cut laminar material.

20 Claims, 2 Drawing Sheets

METHOD FOR THE MANUFACTURE OF AN IMPRESSION-MAKING DEVICE FOR DENTAL USE AND IMPRESSION-MAKING DEVICE THUS OBTAINED

This is a Continuation-in-Part of application Serial No. PCT/IT01/00171 filed Apr. 3, 2001, and the entire disclosure of this prior application is considered to be part of the disclosure of the accompanying application and is hereby incorporated by reference therein.

TECHNICAL FIELD

The invention relates to a process for the manufacture of an impression-making spoon for dental use and to an impression-making spoon obtained using said method.

For the manufacture of dental prostheses, tooth-correction apparatus and the like, impressions of the dental arches are normally made using alginates or other impression materials. Plaster is then cast in the impressions in order to form the model reproducing the characteristics of the patient's teeth. For formation of the impression, the suitably mixed material is applied to a spoon which has a tray for receiving the impression material, with a shape and size such as to accommodate the whole of the patient's arch. The spoon is, moreover, equipped with a fitted handle by means of which the tray containing the impression material is inserted into the oral cavity of the patient.

Spoons with different shapes are used for the upper and lower arches, respectively. The impression-making spoon, which is suitably filled with the impression material, is gripped between the patient's teeth so as to embed all the teeth of one of the two arches in the impression material. Once the necessary hardening time has lapsed, the impression-making spoon is extracted.

STATE OF THE ART

The impression-making spoons are generally made of metal and intended for multiple use. It is therefore necessary to clean and sterilize them thoroughly between use on different patients, among other things and in particular to prevent the spread of contagious diseases which in certain cases may be very dangerous and may be transmitted by means of biological fluids and in particular by blood.

The impression-making spoons which are currently known have a series of fitted elements which make it difficult, if not impossible, to perform correct cleaning and sterilization of said spoon between use on one patient and the next. Only by using spoons made by means of die-casting is it possible to eliminate the undercuts and the superficial niches inside which the paste material, saliva and blood become trapped and which are practically impossible to clean. However, spoons made by means of die-casting have an excessively high cost and for this reason are not popular on the market and in fact are used to a very limited degree.

Normally, therefore, the spoon is made by means of one or more operations using a portion of drawn sheet metal which forms the tray inside which the impression-forming paste is arranged. The handle, by means of which the dentist manipulates the spoon, is joined to the tray by means of welding. This results, on the one hand, in the drawback that niches which cannot be reached during washing and sterilization are formed between the handle and the tray body and, on the other hand, in a high production cost owing to the need for several operations in order to achieve the finished product.

OBJECTS OF THE INVENTION

The present invention relates to an impression-making spoon for dental use and to a process for the production thereof, which avoid the drawbacks of conventional spoons.

More particularly, a first object of the present invention is to provide a faster and more economical production process and therefore a more low-cost spoon.

A second object of the present invention consists in providing an impression-making spoon which is more functional and easier to clean and sterilize.

A further object of the present invention is to provide an impression-making spoon in which the impression-forming material is reliably retained inside the tray during separation of the impression from the patient's dental arch.

SUMMARY OF THE INVENTION

These and further objects and advantages, which will become clear to persons skilled in the art from reading of the text below, are obtained using a method in which the tray and the handle of the spoon are made by means of folding of a single sheet of cut laminar material.

More particularly, according to a possible embodiment of the invention, the process comprises the steps of: providing a sheet of cut laminar material with a central portion intended to form the bottom of the tray, a front extension intended to form the handle and two symmetrical side portions intended to form the shoulders of the tray, partially joined to said central portion along curved folding lines; and folding the side portions along said curved folding lines until they are brought into a position approximately perpendicular to the central portion, folding said side portions along a cylindrical surface until they complete the front zone of the tray shoulder.

With the method according to the invention an impression-making spoon for dental use comprising a tray for containing the impression material and a handle for manipulating the spoon is obtained, wherein said handle and said tray are made from a single sheet of cut and folded laminar material. This reduces the cost of the spoon and makes it easier to sterilize. The side portions of the sheet of cut laminar material (typically sheet steel) which form the side shoulders of the tray may be welded together along their edges arranged end-to-end and along the bottom edge of the tray. However, this is not essential. The absence of a weld, in addition to providing a product which has a lower cost and is safer from a hygiene point of view, results in two further advantages: firstly, the slit which remains between the shoulders and the bottom of the tray helps retain the impression material when forming said impression. In this way it is ensured that the impression does not become detached from the spoon when the latter is extracted from the patient's teeth. Secondly, the shoulders which are not welded together and partially separated from the bottom of the tray allow adaptation, by means of plastic deformation, of the shape of the tray to the configuration of dental arches of patients who have projecting incisors. The slit which remains between the various portions of the tray bottom and shoulders arranged end-to-end has a depth equal to the thickness of the sheet metal forming the spoon and is accessible on both sides. This avoids any hygiene and sterilization-related problems.

Further advantageous features and embodiments of the process and the product according to the present invention are described in the accompanying claims.

BRIEF DESCRIPTION OF THE DRAWINGS

The invention will be better understood with reference to the description and the accompanying drawing which shows a practical non-limiting example of said invention. In said drawing.

DETAILED DESCRIPTION OF A PREFERRED EMBODIMENT OF THE INVENTION

Figure 1:
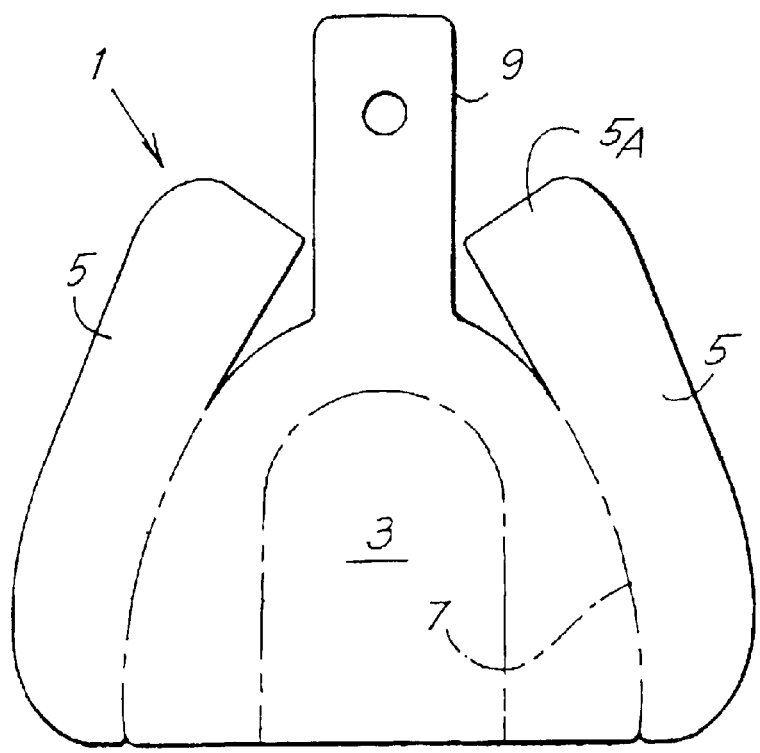
FIG. 1 shows a developed plan view of the cut laminar material from which the impression-making spoon is formed.
Figure 2:
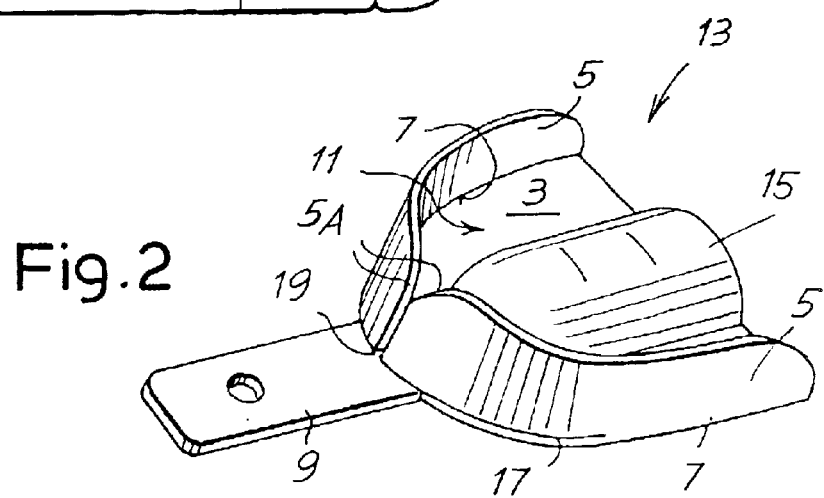
FIGS. 2 and 3 show two perspective views, from, two different angles, of the impression-making spoon obtained using the cut laminar material according to FIG. 1.
Figure 3:
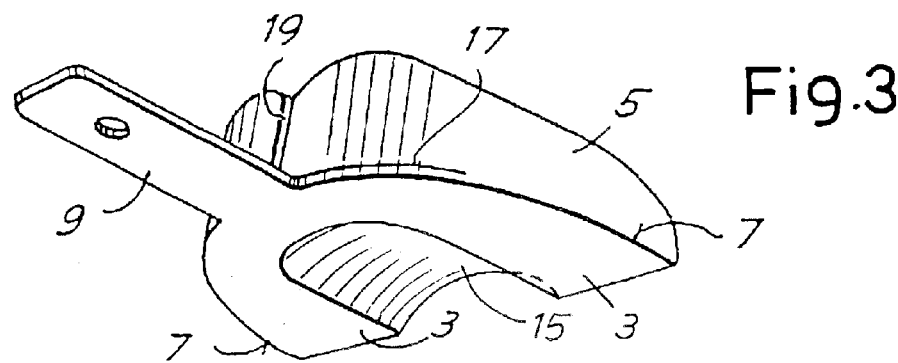

A first embodiment of the invention is shown in FIGS. 1 to 3.

The semi-finished starting material for the production of the impression-making spoon is a sheet of cut laminar material which is generically indicated by 1 and shown in FIG. 1. The laminar sheet has a central portion 3 which is intended to form the bottom of the tray for application of the impression material. Two symmetrical side portions 5, which are joined to the central portion 3 along a folding line 7, extend laterally with respect to the central portion 3. At the front the central portion 3 is extended by a front extension 9 intended to form the handle for gripping and manipulating the spoon.

The impression-making spoon is obtained by means of folding of the cut sheet metal shown in FIG. 1. More particularly, the side portions 5 are folded along the folding lines 7 until they reach a position approximately perpendicular to the central portion 3. Moreover, the zone of each side portion 5 not joined along the line 7 to the central portion 3 is folded along a cylindrical surface so that the two ends 5A of the two side portions 5 are arranged end-to-end in the front zone of the spoon, opposite the handle.

The result of these plastic deformation operations is illustrated in FIGS. 2 and 3. The side portions 5 folded and curved along the cylindrical surface form the side and front shoulder of the tray—generically indicated by 11—of the spoon 13. The handle formed by the extension 9 extends underneath the shoulders, opposite the edges 5A of the side portions 5 arranged end-to-end. In the example illustrated, the central portion 3 has been drawn centrally so as to obtain a central rounded portion 15 corresponding to the palate. In the case where the spoon is used for impressions of the lower arch, the tray will have a free central zone for the patient's tongue.

A slit 17, which may have dimensions, for example, of about 0.5 mm, remains between each side portion 5 and the central portion 3. A similar slit 19 is formed between the edges 5A of the side portions 6 arranged end-to-end. These slits may be closed by means of welding. However, in order to avoid a further step in the production cycle, this welding operation may be omitted. Thus, further advantages are obtained, i.e.:

greater hygiene, since the weld bead has rough surfaces which are difficult to clean and sterilize;

the possibility of plastically deforming the front edges of the side portions 5 so as to adapt the spoon to particularly difficult tooth shapes (incisors which project greatly);

the slits 17, 19 form zones for retaining the impression material which thus adheres more tightly to the tray and does not tend to be separated from the latter during extraction from the oral cavity. The provision of retaining tongues or cavities along the bottom or the shoulders of the tray 11, as is normally required in conventional impression-making spoons, thus becomes superfluous.

The thickness of the metal sheet forming the spoon is such that the depth of the slits 17 and 19 is limited. Since they are accessible on both sides, said slits may be easily cleaned and sterilized, unlike the cavities and the undercuts which are formed, for example, between the bottom surface of the tray and the handle in conventional spoons made as two parts.

The spoon obtained from plastic deformation of the metal sheet according to FIG. 1 may be further finished so as to eliminate the sharp edges (if not eliminated during the previous cutting operation), polished or in any case treated using methods known per se.

Figure 4:
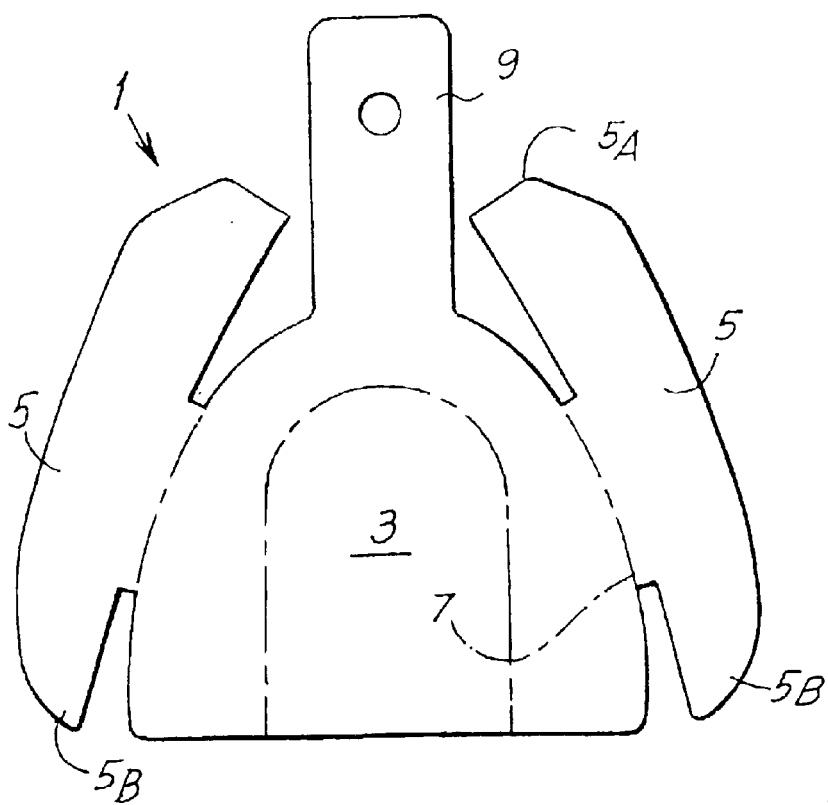
FIGS. 4–6 show three views similar to those of FIGS. 1–3 of a slightly modified and improved embodiment.
Figure 5:
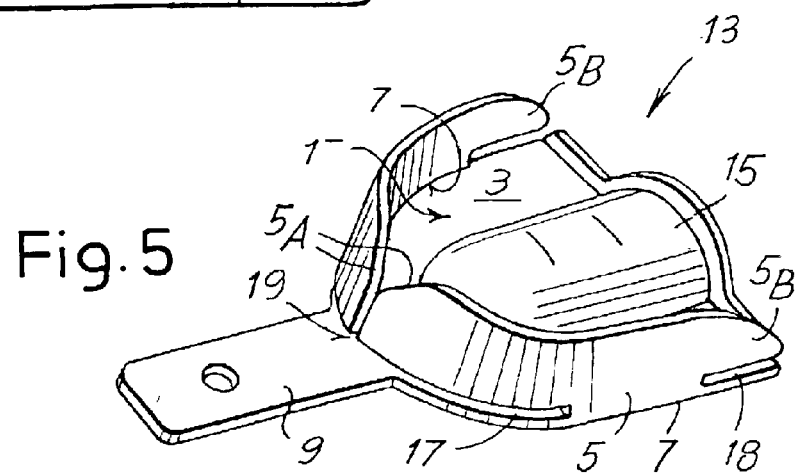
Figure 6:
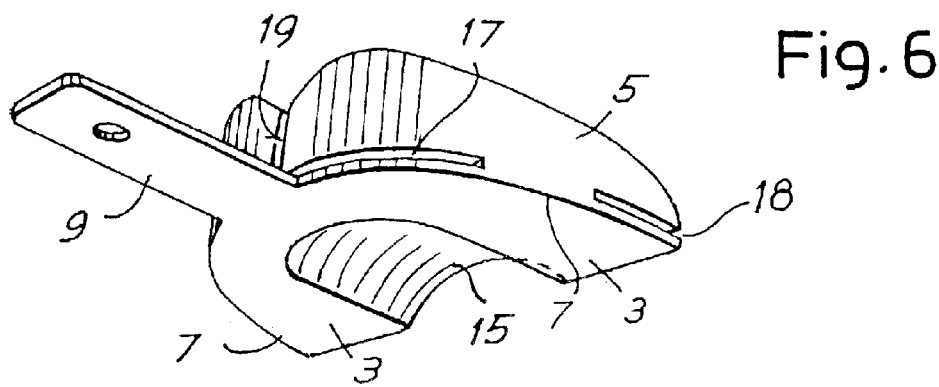

FIGS. 4–6 show a modified embodiment of the spoon according to the invention. Same reference numbers as in FIGS. 1 to 3 are used for identical or corresponding parts.

Also in this case, the semi-finished starting material for the production of the impression-making spoon is a sheet of cut laminar material which is generically indicated by 1 and shown in FIG. 4. The laminar sheet has a central portion 3 which is intended to form the bottom of the tray for application of the impression material. Two symmetrical side portions 5, which are joined to the central portion 3 along a folding line 7, extend laterally with respect to the central portion 3. The folding line 7 extends only along a central section of the portion 5, the latter projecting frontally and rearwardly at 5A and 5B beyond the folding line.

At the front the central portion 3 is extended by a front extension 9 intended to form the handle for gripping and manipulating the spoon.

The impression-making spoon is obtained by means of folding of the cut sheet metal shown in FIG. 4. More particularly, the side portions 5 are folded along the folding lines 7 until they reach a position approximately perpendicular to the central portion 3. Moreover, the front zone of each side portion 5 not joined along the line 7 to the central portion 3 is folded along a cylindrical surface so that the two ends 5A of the two side portions 5 are arranged end-to-end in the front zone of the spoon, opposite the handle.

The result of these plastic deformation operations is illustrated in FIGS. 5 and 6. The side portions 5 folded and curved along the cylindrical surface form the side and front shoulder of the tray—generically indicated by 11—of the spoon 13. The handle formed by the extension 9 extends underneath the shoulders, opposite the edges 5A of the side portions 5 arranged end-to-end. The rear edges 5B of the side portions 5 are separated from the central body 3 along slits 18, Corresponding slits 17 are provided between each side portion 5 and the central portion 3 in the front area of the spoon. The slits 17 and 18 may have a width of between 0,5 an 3 mm, preferably 1 mm.

A similar slit 19 is formed between the edges 5A of the side portions 6 arranged end-to-end. These slits may be closed by means of welding. However, in order to avoid a further step in the production cycle, this welding operation may be omitted. Additionally, if the slits 17 and 18 remain open, they allow for the shape of the spoon to be adapted to the shape of the dental arch of each single patient. For example the front ends of the side portions 5 can be widened in order to adapt to,the front teeth of a patient, while thanks to the slits 18 the back part of the side portions 5 can be adapted to take account of variable shapes of the molar teeth of the patient.

In the example illustrated in FIGS. 3 to 6, the central portion 3 has been drawn centrally so as to obtain a central rounded portion 15 corresponding to the palate. In the case where the spoon is used for impressions of the lower arch, the tray will have a free central zone for the patient's tongue.

The slits 17, 18 and 19 are sufficiently wide and accessible on both sides and allow for safe cleaning and sterilization.

It is understood that the drawing shows only one example provided merely by way of a practical demonstration of the invention, the forms and arrangements of said invention being subject to variation without thereby departing from the scope of the idea underlying said invention. The presence of any reference numbers in the accompanying claims is intended to facilitate reading of the claims with reference to the description and to the drawing and does not limit the scope of protection represented by the claims.

What is claimed is:

1. A method for the manufacture of an impression-making spoon for dental use, adapted to accommodate the whole of a teeth arch, comprising: a tray for the impression-forming material, with a bottom and a shoulder; and a handle for manipulating the spoon; wherein said tray and said handle are formed by means of folding of a single sheet of cut laminar material with a central portion intended to form the bottom of the tray, a extension intended to form the handle and two symmetrical side portions intended to form the shoulders of the tray, characterized by:

providing said sheet of laminar material with said two symmetrical side portions partially joined to said central portion along curved folding lines and having zones not joined to the central portion, each of said zones ending with a respective edge; folding the side portions along said curved folding lines until they are brought into a position approximately perpendicular to the central portion; and folding the zones of said side portions which are not joined to said central portion along a cylindrical surface until they complete the front zone of the tray shoulder by bringing said edges of the side portions in an end-to-end arrangement in the front zone of the spoon, opposite said handle.

2. A method as claimed in claim 1, characterized by the fact of welding the side portions together along the respective edges arranged end-to-end and/or to said central portion.

3. An impression-making spoon for dental use adapted to accommodate the whole of an arch, comprising:

a tray for containing the impression material, with a bottom and a shoulder;

and a handle for manipulating the spoon, wherein said handle and said tray are made from a single sheet of laminar material which is cut and folded, characterized in that said shoulder is formed by two side portions having two edges arranged end-to-end in the front zone of the spoon, above the handle.

4. An impression-making spoon as claimed in claim 3, characterized in that said two side portions are connected to said bottom portion along two curved folding lines and that said side portions are curved along a cylindrical surface to form said front zone of the tray shoulder.

5. An impression-making spoon as claimed in claim 4, characterized in that said side portions are partially separated from the bottom portion along a slit in the front zone of the tray and are moreover separated from each other along the respective edges arranged end-to-end.

6. An impression-making spoon as claimed in claim 4, characterized in that said side portions forming said shoulder are welded together and/or to the bottom portion of the tray.

7. An impression-making spoon as claimed in claim 3, characterized in that said sheet of laminar material is a metal sheet.

8. An impression-making spoon as claimed in claim 3, characterized in that said side portions are partially separated from the bottom portion along a slit in the front zone of the tray and are moreover separated from each other along the respective edges arranged end-to-end.

9. An impression-making spoon as claimed in claim 3, characterized in that said side portions forming said shoulder are welded together and/or to the bottom portion of the tray.

10. A method for the manufacture of an impression-making spoon for dental use, adapted to accommodate the whole of a teeth arch, comprising a tray with a bottom and side shoulders, and a handle, said method including the steps of:

providing a sheet of laminar material with two symmetrical side portions partially joined to a central portion along curved folding lines and each having a front zone ending with a respective front edge;

folding the side portions along said curved folding lines;

folding said front zone of each said side portions bringing said front edges in an end-to-end arrangement in the front zone of the spoon, opposite said handle.

11. Method according to claim 10, wherein said handle and said tray are formed by a single sheet of laminar material.

12. Method according to claim 11, wherein each of said side portions is provided with a rear zone separated from the central portion and deformable with respect to said central portion.

13. Method according to claim 10, wherein each of said side portions is provided with a rear zone separated from the central portion and deformable with respect to said central portion.

14. An impression-making spoon for dental use adapted to accommodate the whole of an arch, comprising a tray, with a bottom and a shoulder, wherein said tray, bottom and shoulder comprise an integrated one-piece sheet material element and further comprising a handle; wherein said shoulder is formed by two side portions of said sheet material being folded and having two front edges arranged end-to-end in a front zone of the spoon, above the handle.

15. An impression-making spoon as claimed in claim 14, characterized in that said sheet of laminar material is a single piece metal sheet.

16. An impression-making spoon as claimed in claim 14, wherein said handle and said tray are made from a single sheet of laminar material which is cut and folded.

17. An impression-making spoon as claimed in claim 16, wherein said two side portions are connected to said bottom portion along two curved folding lines and wherein said front zones of said side portions are curved along a cylindrical surface to form said front zone of the tray shoulder, each of said front zones being separated from said bottom along a slits and being separated from each other along respective front edges arranged end-to-end.

18. An impression-making spoon as claimed in claim 17, wherein each of said side portions has a rear zone which is separated from said bottom along a slit.

19. An impression-making spoon as claimed in claim 14, wherein said two side portions are connected to said bottom portion along two curved folding lines and wherein said front zones of said side portions are curved along a cylindrical surface to form said front zone of the tray shoulder, each of said front zones being separated from said bottom along a slits and being separated from each other along respective front edges arranged end-to-end.

20. An impression-making spoon as claimed in claim 19, wherein each of said side portions has a rear zone which is separated from said bottom along a slit.

* * * * *